US006558733B1

(12) United States Patent
Hossainy et al.

(10) Patent No.: US 6,558,733 B1
(45) Date of Patent: May 6, 2003

(54) METHOD FOR ETCHING A MICROPATTERNED MICRODEPOT PROSTHESIS

(75) Inventors: Syed F. A. Hossainy, Fremont, CA (US); Li Chen, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 45 days.

(21) Appl. No.: 09/697,104

(22) Filed: Oct. 26, 2000

(51) Int. Cl.[7] .............................. B05D 1/32; B05D 3/10; B05D 7/22; A61L 27/00; A61L 33/00
(52) U.S. Cl. ...................... 427/2.24; 427/2.1; 427/2.28; 427/534; 427/555; 427/556; 427/554; 427/154; 427/155; 427/156; 427/282; 427/287; 427/271; 427/272; 427/273; 427/300; 427/307; 216/8; 216/9; 216/10; 216/41; 216/44; 216/45; 216/56; 216/94; 216/106; 216/108; 216/109
(58) Field of Search ................. 427/2.1, 2.24, 427/2.28, 534, 554, 555, 556, 154, 155, 156, 282, 287, 271, 272, 273, 300, 307; 216/8, 9, 10, 41, 44, 45, 56, 94, 106, 108, 109

(56) References Cited

U.S. PATENT DOCUMENTS

| 3,586,999 A | * | 6/1971 | Southgate | 372/43 |
|---|---|---|---|---|
| 4,006,270 A | * | 2/1977 | Morgan | 216/65 |
| 4,101,984 A | | 7/1978 | MacGregor | 3/1.5 |
| 4,459,252 A | | 7/1984 | MacGregor | 264/64.9 |
| 5,059,211 A | | 10/1991 | Stack et al. | 606/198 |
| 5,163,952 A | | 11/1992 | Froix | 623/1 |
| 5,306,286 A | | 4/1994 | Stack et al. | 606/198 |
| 5,328,471 A | | 7/1994 | Slepian | 604/101 |
| 5,443,500 A | | 8/1995 | Sigwart | 623/1 |
| 5,514,154 A | | 5/1996 | Lau et al. | 606/195 |
| 5,527,337 A | | 6/1996 | Stack et al. | 606/198 |
| 5,569,295 A | | 10/1996 | Lam | 606/198 |
| 5,605,696 A | | 2/1997 | Eury et al. | 424/423 |

(List continued on next page.)

FOREIGN PATENT DOCUMENTS

| EP | 0 850 651 | 1/1998 |
|---|---|---|
| EP | 0 875 218 | 4/1998 |
| JP | 11299901 | 2/1999 |
| WO | WO90/01969 | 3/1990 |
| WO | WO96/32907 | 10/1996 |
| WO | WO98/23228 | 6/1998 |
| WO | WO99/16386 | 4/1999 |

OTHER PUBLICATIONS

Barth et al., *Low Dose of Antitumor Agents Prevents Smooth Muscle Cell Proliferation After Endothelial Injury*, JACC 13(2):252A (Abstract) (1989).

Primary Examiner—Shrive P. Beck
Assistant Examiner—Jennifer Kolb Michener
(74) Attorney, Agent, or Firm—Cameron, Kerrigan, Squire, Sanders & Dempsey, L.L.P.

(57) ABSTRACT

An implantable prosthesis, for example a stent, is provided having one or more micropatterned microdepots formed in the stent. Depots are formed in the prosthesis via chemical etching and laser fabrication methods, including combinations thereof. They are formed at preselected locations on the body of the prosthesis and have a preselected depth, size, and shape. The depots can have various shapes including a cylindrical, a conical or an inverted-conical shape. Substances such as therapeutic substances, polymeric materials, polymeric materials containing therapeutic substances, radioactive isotopes, and radiopaque materials can be deposited into the depots.

15 Claims, 5 Drawing Sheets

U.S. PATENT DOCUMENTS

| | | | |
|---|---|---|---|
| 5,700,286 A | 12/1997 | Tartaglia et al. | 623/1 |
| 5,707,385 A | 1/1998 | Wiiliams | 606/192 |
| 5,713,949 A | 2/1998 | Jayaraman | 623/1 |
| 5,741,429 A * | 4/1998 | Donadio et al. | 216/10 |
| 5,749,880 A | 5/1998 | Banas et al. | 606/198 |
| 5,766,238 A | 6/1998 | Lau et al. | 623/1 |
| 5,766,710 A | 6/1998 | Turnlund et al. | 428/36.1 |
| 5,769,883 A | 6/1998 | Buscemi et al. | 623/1 |
| 5,824,455 A * | 10/1998 | Komatsu et al. | 216/51 |
| 5,843,172 A | 12/1998 | Yan | 623/1 |
| 5,873,904 A | 2/1999 | Ragheb et al. | 623/1 |
| 5,902,266 A * | 5/1999 | Leone et al. | 604/508 |
| 5,916,234 A | 6/1999 | Lam | 606/198 |
| 5,951,881 A | 9/1999 | Rogers et al. | 216/41 |
| 6,120,536 A | 9/2000 | Ding et al. | 623/1.43 |
| 6,120,847 A | 9/2000 | Yang et al. | 427/335 |
| 6,203,732 B1 * | 3/2001 | Clubb et al. | 164/464 |
| 6,206,915 B1 | 3/2001 | Fagan et al. | 623/1.42 |
| 6,287,628 B1 | 9/2001 | Hossainy et al. | 427/2.3 |
| 6,312,459 B1 * | 11/2001 | Huang | 623/1.15 |
| 6,379,381 B1 | 4/2002 | Hossainy et al. | 623/1.42 |
| 6,395,326 B1 * | 5/2002 | Castro et al. | 427/2.24 |

\* cited by examiner

METHOD FOR ETCHING A MICROPATTERNED MICRODEPOT PROSTHESIS

FIELD OF THE INVENTION

This invention relates generally to implantable devices, such as expandable intraluminal prosthesis. More particularly, this invention relates to an implantable prosthesis having a plurality of micropatterned microdepots formed in the device to deliver fluid to tissues. Moreover, the present invention relates to a method of fabricating micropatterned microdepots in such a device.

BACKGROUND OF THE INVENTION

A variety of surgical procedures and medical devices are currently used to relieve intraluminal constrictions caused by disease or tissue trauma. An example of one such procedure is percutaneous transluminal coronary angioplasty (PTCA). PTCA is a catheter-based technique whereby a balloon catheter is inserted into a blocked or narrowed coronary lumen of the patient. Once the balloon is positioned at the blocked lumen or target site, the balloon is inflated causing dilation of the lumen. The catheter is then removed from the target site thereby allowing blood to freely flow through the unrestricted lumen.

Although PTCA and related procedures aid in alleviating intraluminal constrictions, such constrictions or blockages reoccur in many cases. The cause of these recurring obstructions, termed restenosis, is due to the body's immune system responding to the trauma of the surgical procedure. As a result, the PTCA procedure may need to be repeated to repair the damaged lumen.

Stents or drug therapies, either alone or in combination with the PTCA procedure, are often used to avoid or mitigate the effects of restenosis at the surgical site. In general, stents are small, cylindrical devices whose structure serves to create or maintain an unobstructed opening within a lumen. The stents are typically made of, for example, stainless steel, nitinol, or other materials and are delivered to the target site via a balloon catheter. Although the stents are effective in opening the stenotic lumen, the foreign material and structure of the stents themselves may exacerbate the occurrence of restenosis or thrombosis.

Drugs or similar agents that limit or dissolve plaque and clots are used to reduce, or in some cases eliminate, the incidence of restenosis and thrombosis. The term "drug(s)," as used herein, refers to all therapeutic agents, diagnostic agents/reagents and other similar chemical/biological agents, including combinations thereof, used to treat and/or diagnose restenosis, thrombosis and related conditions. Examples of various drugs or agents commonly used include heparin, hirudin, antithrombogenic agents, steroids, ibuprofen, antimicrobials, antibiotics, tissue plasma activators, monoclonal antibodies, and antifibrosis agents.

Since the drugs are applied systemically to the patient, they are absorbed not only by the tissues at the target site, but by all areas of the body. As such, one drawback associated with the systemic application of drugs is that areas of the body not needing treatment are also affected. To provide more site-specific treatment, stents are frequently used as a means of delivering the drugs exclusively to the target site. The drugs are suspended in a tissue-compatible polymer, such as silicone, polyurethane, polyvinyl alcohol, polyethylene, polyesters, hydrogels, hyaluronate, various copolymers and blended mixtures thereof. The polymer matrix is applied to the surfaces of the stent generally during the manufacture of the stent. By positioning the stent at the target site, the drugs can be applied directly to the area of the lumen requiring therapy or diagnosis.

In addition to the benefit of site-specific treatment, drug-loaded stents also offer long-term treatment and/or diagnostic capabilities. These stents include a biodegradable or absorbable polymer suspension that is saturated with a particular drug. In use, the stent is positioned at the target site and retained at that location either for a predefined period or permanently. The polymer suspension releases the drug into the surrounding tissue at a controlled rate based upon the chemical and/or biological composition of the polymer and drug.

The above-described devices and methods for treatment of restenosis and thrombosis, and other similar conditions not specifically described, offer many advantages to potential users. However, it has been discovered that such devices and methods may be deficient in their current drug-loading and drug-delivery characteristics. In particular, the amount or volume of drug capable of being delivered to the target site may be insufficient due to the limited surface area of the stent.

In view of the above, it is apparent that there is a need to provide a fluid delivery device offering increased drug loading capabilities for stents and other prosthetic devices. It is also desirable that the drug-delivery device allows fluids to be released at variable and/or independent rates. There is also a need to provide a method of manufacturing such an improved fluid delivery device that is convenient, efficient and cost effective.

SUMMARY OF THE INVENTION

In accordance with various aspects of the present invention, an implantable prosthesis, one example of which includes a stent, has a body structure that is generally cylindrical in shape with a hollow bore that extends longitudinally through the body structure. The outer surface of the prosthesis is capable of contacting an inner lumen surface of a passageway. In addition, the body structure of the prosthesis has one or more micropatterned microdepots formed therein. The depots have an open end, a closed end, a diameter and a depth that is less than the thickness of the body structure of the prosthesis. In general, the depots have an inverted-conical shape, whereby the diameter of the depots decreases from the closed end to the open end of the depots.

Another aspect of the present invention is a method of forming pores on an implantable prosthesis. The method is applicable not only to the above-described prosthesis, but also to any implantable prosthesis having a surface. The method includes applying a first fluid onto the surface of the prosthesis, the first fluid forms a protective coating on the surface. A mask having transparent and opaque area is generated. In general, the transparent areas represent the pores that are to be applied to the prosthesis. The mask is illuminated with light so that the light passes through the transparent areas forming exposed metal areas on the surface of the prosthesis. A second fluid that dissolves the exposed metal areas to a predetermined depth, thereby forming a well, is also applied to the prosthesis. The second fluid is removed such that a quantity of fluid remains within the well. The second fluid is used to expand the size and volume of the pore. After achieving the desired pore profile, the second fluid is removed and the prosthesis is rinsed in a third fluid to remove the protective coating on the surface of the prosthesis.

In accordance to another embodiment, an alternative method of forming pores on an implantable prosthesis is disclosed. The method includes applying a first fluid onto the prosthesis so that the first fluid forms a protective coating on the surface of the prosthesis. A laser is used to selectively ablate portions of the protective coating. In general, the laser drills into the prosthesis and forms one or more wells. A second fluid is applied to the prosthesis, causing the well or pore size and volume to expand. After achieving the desired pore profile, the second fluid is removed and the prosthesis is rinsed in a third fluid to remove the protective coating on the surface of the prosthesis.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION OF THE INVENTION

Figure 1:
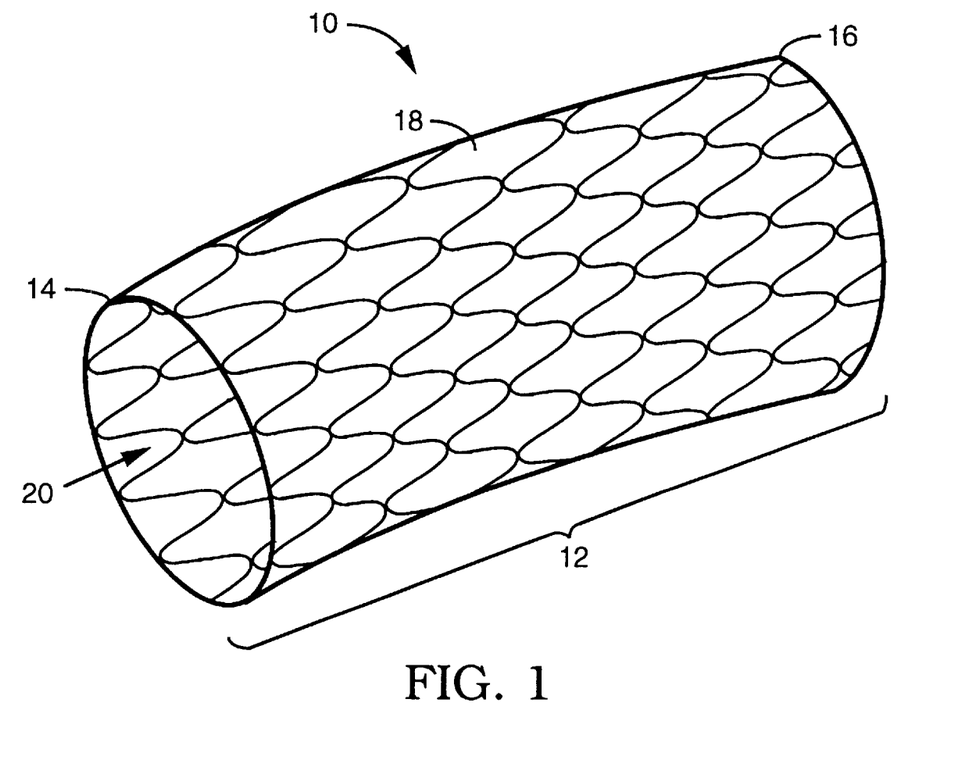
FIG. 1 is a perspective "three" dimensional view of an implantable prosthesis, e.g. stent, in accordance with an embodiment of the present invention.

FIG. 1 illustrates an implantable prosthetic medical device 10. In the spirit of convenience and brevity, the medical device referenced in the text and figures of the present disclosure is a stent 10. However, it should be noted that other medical devices or prosthesis are also within the scope of the claimed invention.

As shown in FIG. 1, the stent 10 is generally cylindrical or tubular in shape or body structure 12 and has a first end 14, a second end 16 and a mid-section 18. In addition, a hollow bore 20 extends longitudinally through the body structure 12 of the stent 10. The structure of the stent 10 allows it to be inserted into and physically hold open an anatomical passageway by exerting a radially outward-extending force against the walls or inner lumen surface of the passageway. If desired, the stent 10 can also expand the opening of the lumen to a diameter greater than its original diameter and, thereby, increase fluid flow through the lumen.

Figure 2:
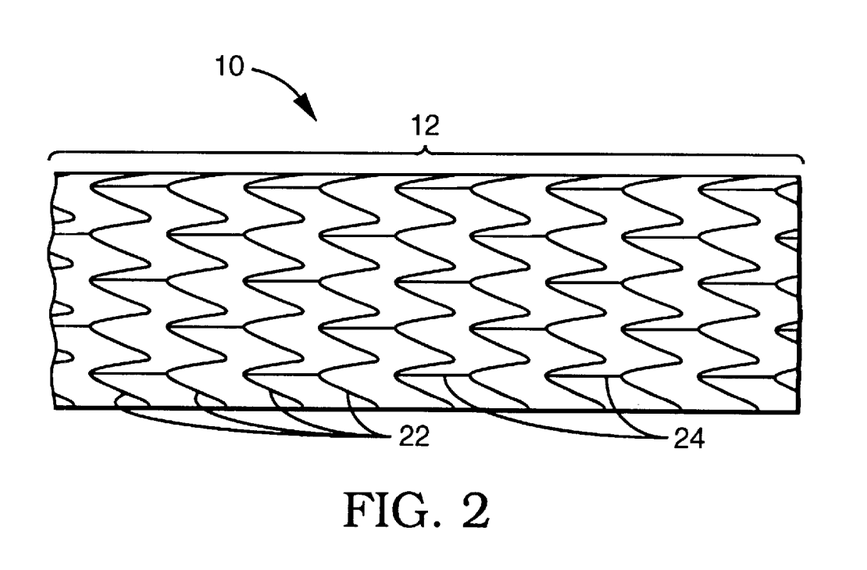
FIG. 2 is a side view of filaments and interconnecting elements of an implantable prosthesis in accordance with FIG. 1.
Figure 3:
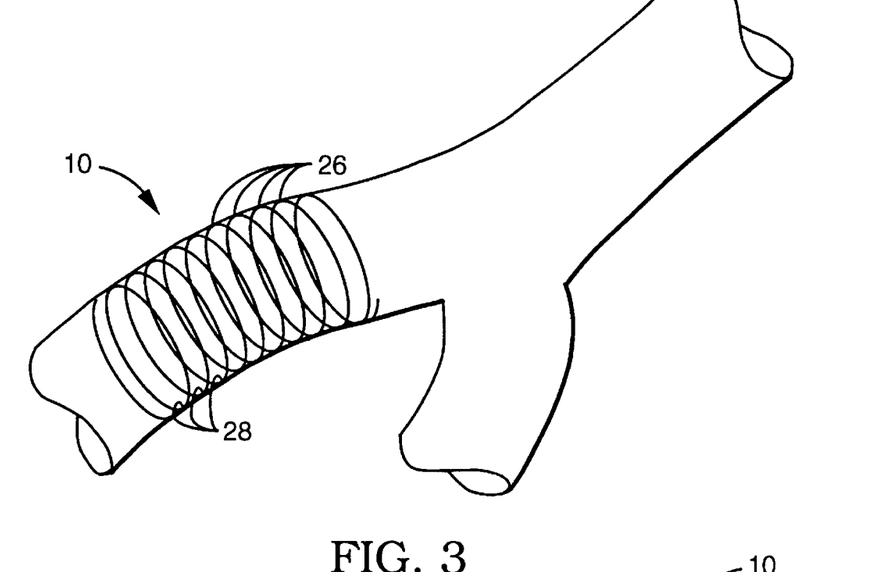
FIG. 3 illustrates an implantable prosthesis inserted into the lumen of a patient.

Referring to FIG. 2, the stent 10 includes one or more resiliently flexible filament-type elements 22 that make up the body 12 of the stent 10. The individual shape of the preformed filaments 22 may be straight, sinusoidal, V-shaped, or any other of a variety of patterns and shapes not disclosed herein. The filaments 22 are radially expandable and interconnected by connecting elements 24 that are disposed between adjacent filaments 22. As with the filaments 22, the interconnecting elements 24 may also have a variety of shapes and patterns including, but not limited to, circular, oval, straight, curved, etc. Both the filaments 22 and interconnecting elements 24 define the tubular stent 10 body 12 having a lumen contacting surface 26 and an inner surface 28, as shown in FIG. 3.

The filaments 22 and interconnecting elements 24 of the stent 10 are configured to allow the stent 10 to easily expand and contract, thereby facilitating placement of the stent 10 into an insertion device and, ultimately, a lumen of the body. To further enhance stent 10 flexibility, these components are typically fabricated from a metallic material or alloy, such as stainless steel, Nitinol™, gold, or other similar materials and/or combinations of such materials. The diameter of each filament 22 is typically within the range of approximately 0.002 inch ($5.08' \times 10^{-3}$ cm) to 0.008 inch ($20.32 \times 10^{-3}$ cm). Similarly, the diameter for each interconnecting element 24 is approximately within the range of 0.002 inch ($5.08 \times 10^{-3}$ cm) to 0.007 inch ($17.78 \times 10^{-3}$ cm). Overall stent 10 inner diameter, outer diameter and length are approximately within the range of 0.04 inch (0.1016 cm) to 0.16 inch (0.4064 cm), 0.044 inch (0.1118 cm) to 0.18 inch (0.4572 cm), and 0.315 inch (0.8 cm) to 2.559 inch (6.5 cm), respectively. In general, the thickness of the walls of the body structure 12 of the stent 10 range from 0.002 inch ($5.08 \times 10^{-3}$ cm) to 0.010 inch ($25.4 \times 10^{-3}$ cm). The particular configuration of the stent 10, including choice of materials, size, structural characteristics, etc., may vary based upon the location and lumen dimensions of the target area.

Figure 4A:
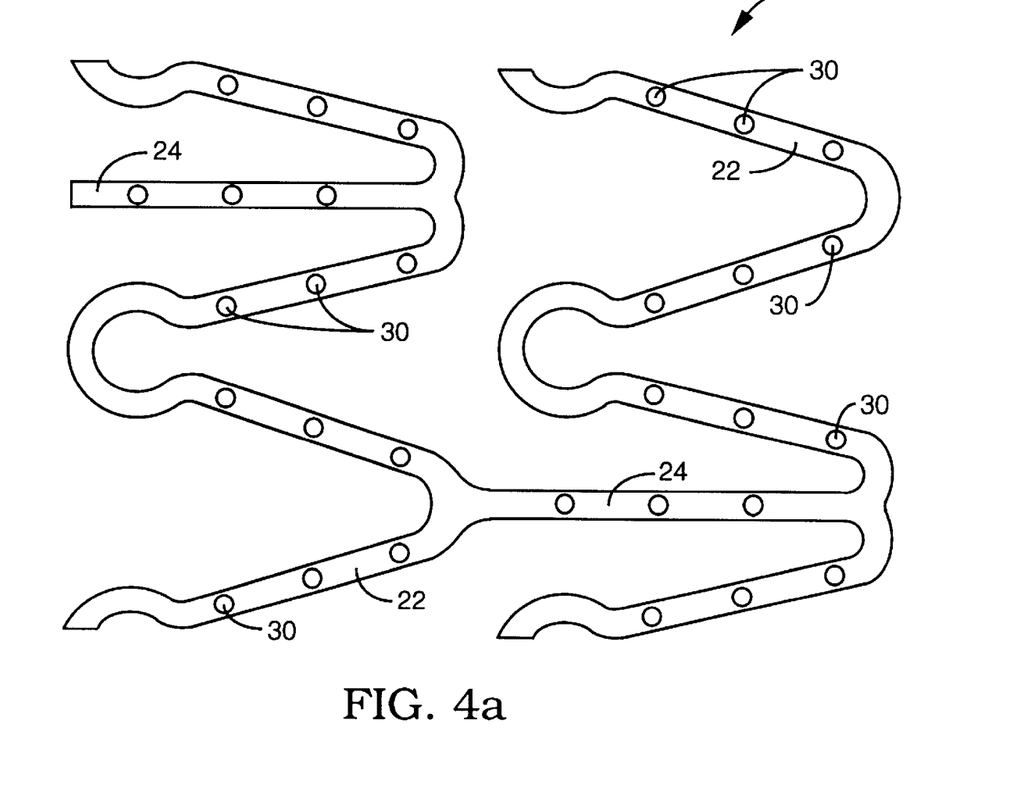
FIGS. 4a and 4b illustrate a portion of an implantable prosthesis having micropatterned microdepots on a surface of the device in accordance with an embodiment of the present invention.
Figure 4B:
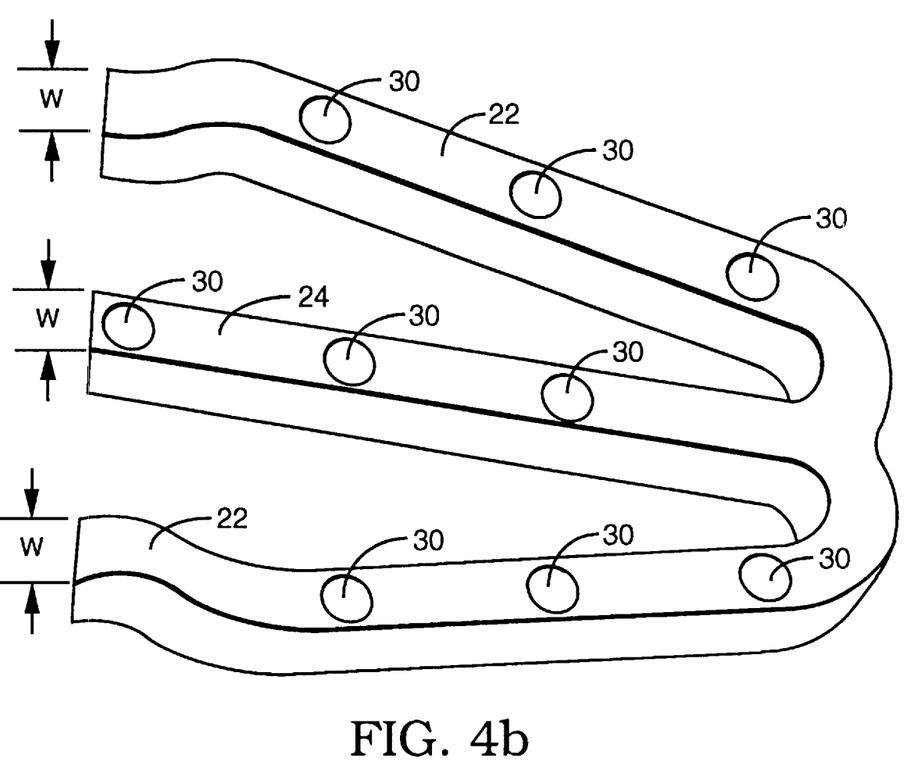

As shown in FIGS. 4a and 4b, one or more microdepots (i.e. depots) or pores 30 are formed on the stent 10. The depots 30 are used to carry a variety of substances including, but not limited to, therapeutic substances, polymers impregnated with therapeutic substances, radioactive isotopes, and radiopaque materials. Examples of therapeutic substances or agents used with the present invention include antineoplastics, antiinflammatory substances, antiplatelets, anticoagulants, fribrinolytics, thrombin inhibitors, antimitotics, and antiproliferatives. Examples of antineoplastics include paclitaxel and docetaxel. Examples of antiplatelets, anticoagulants, fribrinolytics, and thrombin inhibitors include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of suitable antimitotic agents include methotrexate, azathioprine, vincristine, vinblastine, flurouracil, adriamycin, actinomycin D, and mutamycin. Examples of suitable cytostatic or antiproliferative agents include angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. In yet other embodiments, the therapeutic substance is a radioactive isotope for stent 10 usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). While the listed therapeutic substances or agents are well known for preventative and therapeutic utility, the substances are listed by way of example and are not meant to be limiting. Other therapeutic substances which are currently available or that may be developed in the future are equally applicable. The treatment of patients using the above mentioned medicines is well-known to those of ordinary skill in the art.

The location and configuration of the depots 30 vary according to intended usage and application of the prosthesis 10. In one embodiment, depots 30 are evenly distributed throughout the body of the stent 10 and have an equal volume so that tissue in contact with the stent 10 receives an equal distribution of therapeutic substances. In an alternate embodiment, the volume of the depots 30 is greater at each end 14, 16 of the stent 10 compared to the mid-section 18 of the stent 10. For example, in one embodiment, the depots 30 at the ends 14, 16 of the stent 10 carry heparin, whereas the mid-section 18 depots 30 carry methotrexate. Alternate embodiments of stents 10 having different depot patterns, volumes and therapies, configured according to clinical purpose and usage requirements, though not specifically described herein are also included within the scope of the present invention.

Figure 5A:
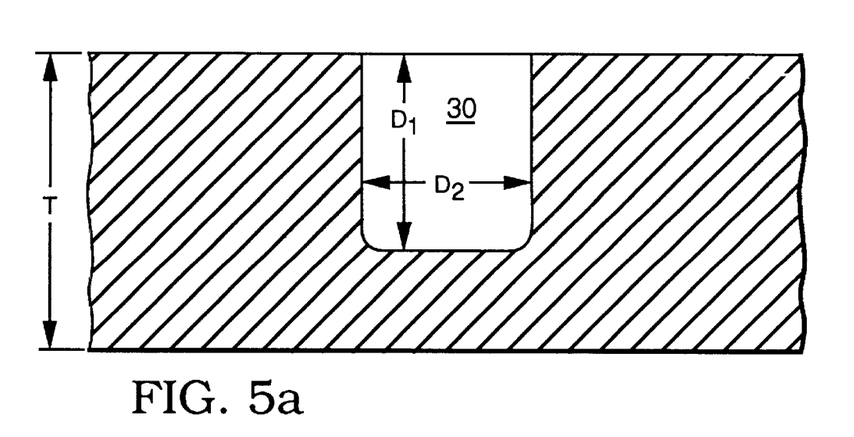
FIGS. 5a and 5b illustrate a cross-sectional view of a microdepot on a surface of a portion of an implantable prosthesis in accordance with FIGS. 4a and 4b, respectively.
Figure 5B:
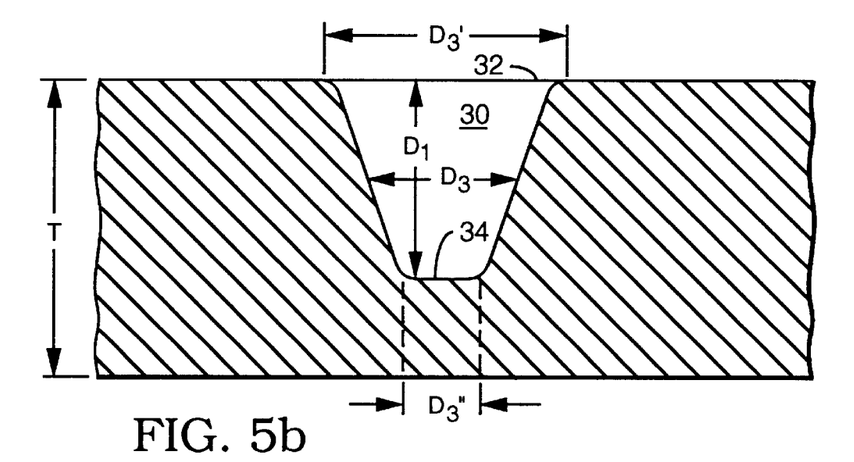

Referring to FIGS. 5*a* and 5*b,* for a stent 10 that carries a therapeutic substance or a polymeric carrier impregnated with a therapeutic substance, a suitable depot or pore 30 depth $D_1$ has a range from about 10% to about 90% of thickness T. Typically a depth not greater than about 50% of thickness T is most suitable. The specific depth $D_1$ of the depots 30 depends on the amount of therapeutic substance that is to be deposited in the depots 30. In an example of a stent 10 that carries a radioactive isotope, depth $D_1$ is typically about 10% to about 80% of thickness T. More specifically, a depth not greater than about 30% of thickness T is suitable.

For a stent 10 that carries a radiopaque material, a suitable depot or pore 30 depth $D_1$ has a range from about 10% to about 90% of thickness T. Typically a depth not greater than about 65% is most suitable. A depth $D_1$ greater than about 65% of the thickness may compromise the structural integrity and mechanical functionality of stent 10. However the upper limit of depth $D_1$ varies depending on the material characteristics such as the hardness of the body 12.

Depots 30 may be formed in a variety of selected geometrical shapes. Referring to FIGS. 4*b* and 5*a,* a depot 30 is a generally cylindrically shaped. A diameter $D_2$ of a cylindrical depot 30 typically has a range from about 10% to about 90% of filament 22 width W, although the diameter $D_2$ is usually not greater than about 80% of width W. The specific diameter $D_2$ depends on the application and purpose of the depots 30. The upper limit of diameter $D_2$ varies depending on the material characteristics such as hardness of the stent body 12.

An alternative example of a depot 30, illustrated in FIG. 5*b,* is generally conical in shape. The conical shaped depot 30 has an open end 32 and a closed end 34. The open end 32 is the end that contacts a surface of a tissue. A diameter $D_3$ of conical shaped depot 30 is shown to increase from closed end 34 to open end 32. The largest diameter $D_3'$ at the open end 32 of the conical shaped depot 30 has a range from about 10% to about 80% of the filament width W. Generally, the largest diameter $D_3'$ is not greater than about 70% of width W. The smallest diameter $D_3''$ at the closed end 34 of the conical shaped depot 30 has a range from about 5% to about 70% of the width W. Generally, the smallest diameter $D_3''$ is not greater than about 60% of width W. The size of opening that contacts the surface of a tissue determines the rate at which a therapeutic substance is released once the stent 10 is implanted at the desired location of treatment.

The depth $D_1$ and diameters $D_2$ and $D_3$ of the individual depots 30 formed on the stent 10 can vary relative to one another. In one example, depot volume can be selectively controlled along different portions of the stent 10 during stent fabrication, either by selectively varying the volume or making the volume of the depots 30 consistent throughout the body 12 of the stent 10. For some applications, consistent depot volume is important for delivery of a therapeutic substance to insure that the substance is evenly distributed throughout stent 10 and results in consistent application of the therapeutic substance to the tissues in contact with the surface 26 of the stent 10.

A factor for determining the size, geometry, and concentration of depots 30 on the stent 10 is the overall stent 10 porosity. Porosity is the total volume of pores 30 in the body 12 of a stent 10 divided by the total volume of structural material of the stent 10. Porosity determines, the capacity of a substance that can be loaded into a stent 10 of predetermined dimensions. High porosity can adversely affect the structural integrity, strength, and elasticity of the stent 10. Consequently, stent design includes consideration of a tradeoff between strength, on one hand, and stent 10 profile and stent 10 load capacity on the other hand.

The profile or configuration of the individual depots 30 can be modified to increase stent load capacity while maintaining stent 10 strength. In one embodiment, shown in FIG. 6, the depot profile is configured to form an inverted conical shape. The depth $D_1$ of the depot 30 remains the same, as previously described above. The inverted conical-shaped depot 30 has an open end 32 and a closed end 34. The open end 32 is the end that contacts the surface of a tissue. A diameter $D_4$ of the inverted conical-shaped depot 30 is shown to decrease from closed end 34 to open end 32. The largest diameter $D_4''$ at the closed end 34 of the conical shaped depot 30 has a range from about 10% to about 80% of the filament width W. Generally, the largest diameter $D_4''$ is not greater than about 70% of width W. The smallest diameter $D_4'$ at the open end 32 of the conical shaped depot 30 has a range from about 5% to about 70% of the width W. Generally, the smallest diameter $D_4'$ is not greater than about 60% of width W. Controlling the size of the opening that contacts the surface of a tissue also controls the rate at which a therapeutic substance is released once the stent 10 is implanted at the desired location of treatment.

Depots 30 are fabricated in a stent 10 using several illustrative methods. The methods are applicable to the illustrative stents 10 described hereinbefore and also to any type of prosthetic device. In general, depots 30 are formed in a surface of a stent 10 using a multi-step chemical etch process or lasers, such as an excimer laser or a Nd:YAG (neodymium yttrium aluminum garnet) laser.

Chemical etching is a manufacturing technique whereby selected portions of a metal surface are blanked or dissolved away using a chemical etchant or an acid. The desired image to be etched into the metal is generated using conventional techniques that are well known in the art. For example, the desired image for the present device includes one or more micropatterned holes 30 representing the final location of the microdepots 30 on the stent 10 and their resultant diameter.

Figure 7A:
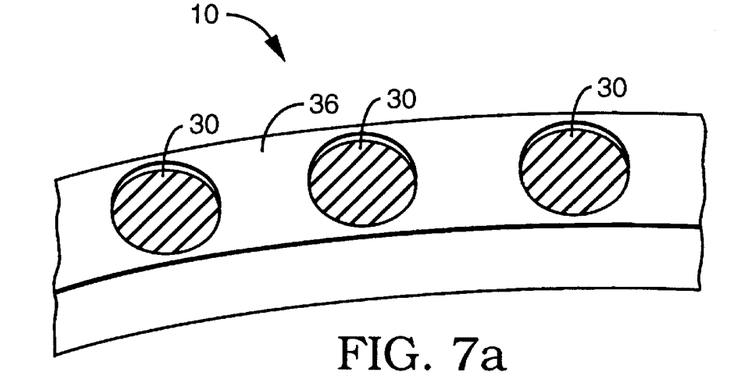
FIG. 7a illustrates a portion of an implantable prosthesis coated with a layer of resist.

Prior to transferring the image, the metal surface of the stent 10 is cleaned and treated with a first solution or fluid to ensure that the image adheres to the metal surface. Generally, the first solution is a type of photoresist, such as Aquamer (manufactured by Aquamer), or SC180 (manufactured by Arch Chemical), or other similar resists. Light from an illumination source passes through a photomask which defines the desired microdepot pattern image. The photomask consists of areas that are completely opaque and complementary areas that are transparent. Some of the light that passes through the mask continues through a lens, which projects an image of the mask pattern onto the stent surface. The photoresist undergoes a chemical reaction upon exposure to light, such as UV light. After exposure, the stent is developed. Thus, the metal surface becomes an exact replica of the desired micropatterned microdepots 30. In particular, all non-depot portions of the surface of the stent 10 are covered with a protective layer 36 of the resist, leaving exposed metal areas at the location of each microdepot 30 as shown in FIG. 7a. The resist serves as a barrier to the etching solutions that are used to literally "eat" the imaged microdepots out of the metal surface, as further described below.

Figure 7B:
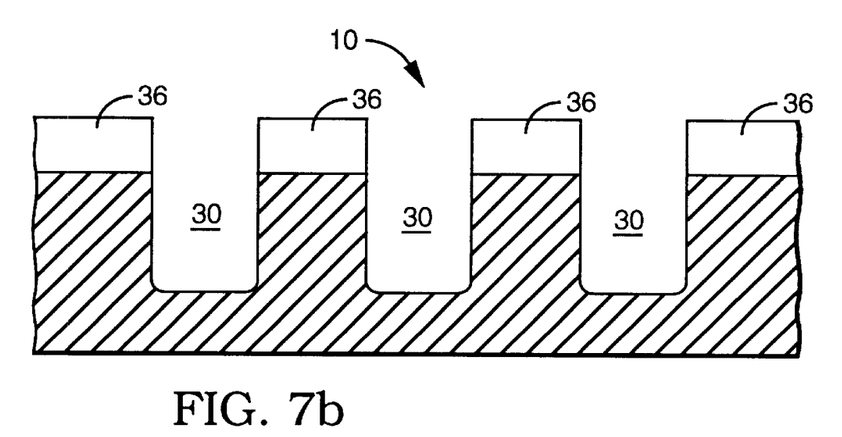
FIG. 7b illustrates resist-coated portions and etched-metal sections of an implantable prosthesis.

The imaged metal is then immersed, sprayed or dipped in a second solution or fluid that selectively dissolves away the exposed portions of metal, as illustrated in FIG. 7b. The second solution may be a chemical, gas or acid including, but not limited to, ferric chloride solution or other similar solutions that dissolve the non-coated metal portions of the stent 10. The length of time that the imaged metal remains in the second solution depends on the desired pore shape and concentration of the solution. After etching, the second solution is removed from the stent 10 via spinning, rotating, shaking, vaporizing or other removal methods.

The prosthesis 10 is subsequently rinsed in a third solution or fluid. The third solution is typically a stripping solution that facilitates removal of the protective coating 36 previously applied to the device 10. Solutions such as methylene chloride or other solutions well known in the art may be used to dissolve the resist. The prosthesis is rinsed in the third solution until all traces of the coating are removed from the stent 10. The third solution is removed from the stent 10 using a technique such as spinning, rotating, shaking, vaporizing or other removal methods. The resultant stent 10, of which a portion is shown in FIGS. 4a–5b, includes the desired micropatterned microdepots 30 formed in its surface. Once the depots 30 are formed in the stent 10, various drugs or therapeutic substances may be loaded into the depots 30.

In one embodiment, the above-described etching technique is performed on a prefabricated prosthetic device, such as a stent 10. In an alternate embodiment, the etching technique is also used on the individual components or raw materials of the device 10. For example, with regard to a stent 10, etching is performed on a flat sheet of material from which stent filaments and interconnecting components are fabricated. The benefits of producing depots 30 on the raw materials of the filaments 22 and interconnecting elements 24 prior to stent assembly include increased manufacturing productivity, reduced fabrication costs, improved processing times, and facilitated manufacturability.

In addition to etching techniques, micropatterned microdepots 30 may also be formed on prosthetic medical devices 10 using lasers. Examples of lasers include UV/excimer lasers and Nd:YAG lasers. UV lasers are ideal for micromaching applications due to the short wavelength, minimal thermal interaction with the material, increased precision and cleanliness of the drilled depots formed using such lasers. As such, these processing characteristics provide high micromachining quality and extreme precision with minimum influence on the surrounding material. Furthemnore, compared to etching techniques, UV lasers offer faster processing times and elimination of environmental and safety problems associated with chemical handling and disposal.

There are several methods by which microdepots 30 are formed on a prosthetic medical device using a laser. In one embodiment, a 20 mJ KrF excimer laser (with a 248 nm wavelength) is used to illuminate a mask having one or more micropatterned microdepots 30. The image is projected onto the surface of the device 10 and the depots or holes 30 are thereby simultaneously drilled a predetermined depth into the material. In an alternate embodiment, a 20 W pulsed Nd:YAG laser beam is brought to focus on the surface of the device 10 and each microdepot 30 is individually drilled to the desired depth and pattern in the material. While the excimer laser is best suited for devices having a fixed hole distribution pattern with a large amount of holes, the Nd:YAG laser offers a useful option for devices having smaller numbers of holes and a flexible hole distribution pattern.

Figure 6:
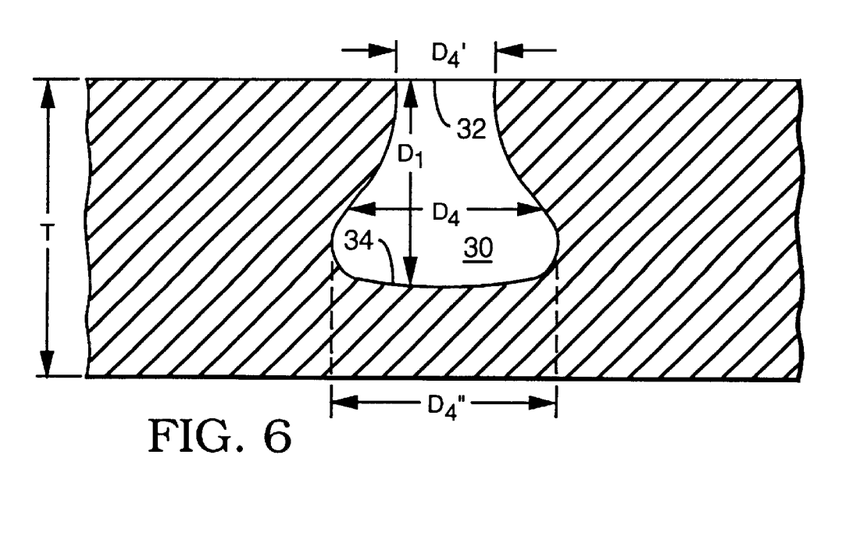
FIG. 6 illustrates a cross-sectional view of a microdepot on a surface of a portion of an implantable prosthesis.

Chemically etched and laser fabricated microdepots 30 produce a generally cylindrical or conical shaped depot profile, as shown in FIGS. 5a and 5b. To increase stent load capacity and selectively control drug release rates, the microdepot profile is modified to generally form an inverted conical shape. As shown in FIG. 6, increasing the diameter of the depot 30 from its open end 32 to its closed end 34 enlarges depot load capacity or volume. There are several methods by which such a microdepot 30 may be fabricated.

Method 1

In one embodiment, microdepots 30 are formed on a stent 10 using chemicals, acids and/or solvents in either gaseous or liquid form. A two-dimensional image or mask representing the desired pattern and open-end 32 or surface diameter of one or more depots 30 on a stent 10 is generated. Prior to transferring the image, the metal surface of the stent 10 is cleaned and treated with a first solution or fluid, via immersing, spinning or dipping, to ensure that the image adheres to the metal surface. Generally, the first solution is a type of photoresist, such as Aquamer (manufactured by Aquamer), SC180 (manufactured by Arch Chemical), or other similar resists. Light from an illumination source passes through the mask which defines the desired microdepot pattern image. The photomask consists of areas that are completely opaque and complementary areas that are transparent. Some of the light that passes through the mask continues through a lens, which projects an image of the mask pattern onto the stent surface. The stent undergoes a chemical reaction upon exposure to light, such as UV light. After exposure, the stent is developed. Thus, the metal surface of the stent 10 becomes an exact replica of the desired micropatterned microdepots 30. In particular, all non-depot portions of the surface of the stent 10 are covered with a protective layer 36 of the first fluid, leaving exposed metal areas at the location of each microdepot 30. The stent 10 is then placed in a chamber and exposed to a second fluid that etches the bare metal areas to a predetermined depth, forming a well.

Figure 8:
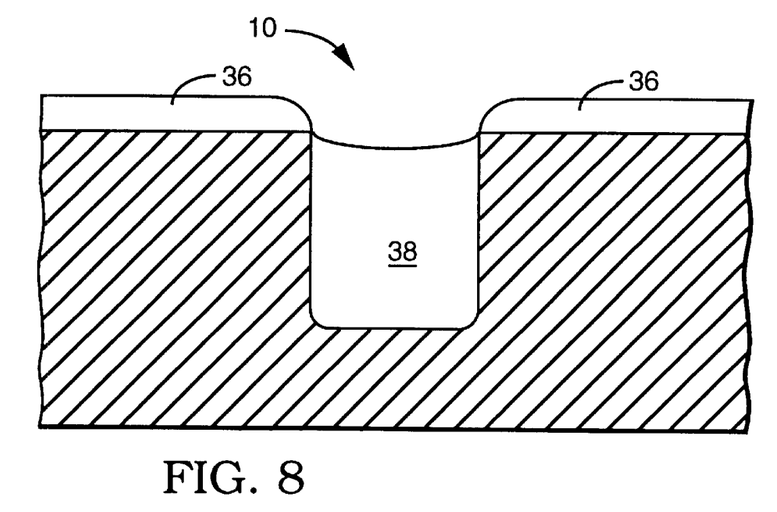
FIG. 8 illustrates a fluid filled depot and resist-coated portions of an implantable prosthesis.

The second fluid is removed from the surface of the stent 10, via spinning, rotating, shaking, vaporizing or other removal methods, to halt the surface-etching process. However, as shown in FIG. 8, a quantity of fluid 38 remaining within the well is allowed to continue to etch the walls of the well, thereby expanding the below-surface pore size and volume.

Once the desired pore profile is attained, the remaining fluid is completely removed from the pore 30 via spinning, rotating, shaking, vaporizing or other removal methods to stop the etching process.

The stent 10 is then rinsed in a third fluid that effectively dissolves the protective coating 36 previously applied to the surface of the stent 10. In general, an ultrasonic cleaning process follows to remove residual fluids and/or debris.

Method 2

In another embodiment, microdepots 30 are formed on a stent 10 using a combination of fluids and lasers. As with the previous method, the surface of the stent 10 is cleaned and covered with a protective coating 36 of a first fluid. The first fluid is applied via immersing, spraying or dipping the stent 10 in the fluid. A mask having transparent and opaque areas representing the location and surface-opening of one or more microdepots 30 is placed on the surface of the stent 10 and illuminated with laser light, such as an excimer laser beam. The mask acts as a stencil allowing the beam of laser light to pass through its transparent portions, while simultaneously blocking the light at its opaque, complementary areas. As such, the laser removes the protective layer from the illuminated portions of the stent surface (corresponding to the microdepot areas), resulting in exposed, bare metal areas on the surface of the stent 10.

The imaged stent is then immersed, sprayed or dipped in a second fluid that selectively etches the bare metal areas to a predetermined depth, forming a well. The fluid is removed from the surface of the stent 10, via spinning, rotating, shaking, or other removal methods, to halt the surface-etching process. However, fluid 38 remaining within the well is allowed to continue to etch the walls of the well, thereby expanding the below-surface pore size and volume.

Once the desired pore profile is attained, the remaining fluid is removed from the pore 30 via spinning, rotating, shaking or other removal methods to stop the etching process.

The stent 10 is then rinsed in a third solution that effectively dissolves the protective coating previously applied to the surface of the stent 10. In general, an ultrasonic cleaning process follows to remove residual fluids and/or debris.

Method 3

In another embodiment, microdepots 30 are formed on a stent 10 using a combination of fluids and lasers. The surface of the stent 10 is covered with a protective coating 36 of a first fluid. The stent 10 is immersed, sprayed or dipped in the first fluid. A laser beam is used to selectively ablate portions of the protective coating 36 covering the surface of the stent 10. As such, the energy from the laser continues to drill into the metal of the stent, thereby forming one or more cylindrical or conical-shaped wells.

The wells are then filled or loaded with a second fluid that etches the walls of the wells, thereby expanding the below-surface depot size and volume. The microdepots 30 may be loaded with fluid using several methods, including dipping, needle injection, spraying or other similar methods.

Once the desired pore profile is attained, the remaining fluid is removed from the pore 30 via spinning, rotating, shaking or other similar removal methods to stop the etching process.

The stent 10 is then rinsed in a third fluid that effectively dissolves the protective coating 36 previously applied to the surface of the stent 10. In general, an ultrasonic cleaning process follows to remove residual fluids and/or debris.

Several examples illustrate various methods for forming micropatterned microdepots 30 on a stent 10. The examples illustrate but do not limit the possible techniques for forming micropatterned microdepots 30.

EXAMPLE 1

As described above, a two-dimensional image representing the desired pattern and open-end 32 or surface diameter of one or more depots 30 on a stent 10 is generated. Prior to transferring the image, the surface of the stent 10 is cleaned and covered with a protective coating 36 of photoresist, such as MICROSTOP (manufactured by Tobler Division, Pyramid Plastics, Inc.). The image is then transferred to the surface of the stent 10 and developed. As a result, all non-depot portions of the surface of the stent 10 are covered with the protective layer 36, leaving exposed metal areas at the location of each microdepot 30. The stent 10 is then placed in a chamber and exposed to ferric chloride solution or other similar solutions that etch the bare metal areas to a predetermined depth, such as 60% of the desired, overall depth, forming a well.

The ferric chloride solution is removed from the surface of the stent 10, via spinning, rotating, shaking, or other removal methods, to halt the surface-etching process. A small quantity of ferric chloride solution remains within the well, continuing to etch the walls of the well. The below-surface pore size and volume are thereby increased. Once the desired pore profile is attained, the remaining ferric chloride solution is completely removed from the pore 30 via spinning, rotating, shaking or other removal methods to stop the etching process.

The stent 10 is then rinsed in methylene chloride or other similar solutions that effectively dissolve the protective coating 36 previously applied to the surface of the stent 10. An ultrasonic cleaning process generally follows to remove residual fluids and/or debris.

EXAMPLE 2

Similar to the previous method, the surface of the stent 10 is cleaned and covered with a protective coating 36 of Miccrostop (manufactured by Tobler Division, Pyramid Plastics, Inc.). A mask representing the location and surface-opening of one or more microdepots 30 is placed on the surface of the stent 10 and illuminated with a 20 mJ excimer laser. The mask acts as a stencil allowing the beam of laser light to pass through its transparent portions, while simultaneously blocking the light at its opaque areas. As such, the laser illuminated portions of the coated surface (i.e. the microdepot areas) are ablated and the coating is removed, resulting in exposed, bare metal areas on the surface of the stent 10. The non-illuminated portions of the stent 10 remain covered with the protective Miccrostop coating 36.

The stent 10 is then placed in a chamber and exposed to ferric chloride solution or other similar solutions that etch the bare metal areas to a predetermined depth, such as 60% of the desired, overall depth, forming a well. The ferric chloride solution is completely removed via spinning, rotating, shaking or other removal methods from the surface of the stent 10 to halt the surface-etching process. A small quantity of ferric chloride solution remains within the well, continuing to etch the walls of the well. The below-surface pore size and volume are thereby increased.

Once the desired pore profile is attained, the remaining ferric chloride solution is completely removed from the pore 30 via spinning, rotating, shaking or other similar methods to stop the etching process. The stent 10 is then rinsed in methylene chloride or other similar solutions that effectively dissolve the protective coating 36 previously applied to the surface of the stent 10. An ultrasonic cleaning process generally follows to remove residual fluids and/or debris.

EXAMPLE 3

The surface of the stent 10 is covered with a protective coating 36 of Miccrostop. A laser beam selectively ablates portions of the protective coating 36 covering the surface of the stent 10. As such, the energy from the laser continues to drill into the metal of the stent 10, thereby forming one or more cylindrical or conical-shaped wells.

The stent 10 is then placed in a chamber and exposed to ferric chloride solution or other similar solutions that etch the bare metal areas to a predetermined depth, such as 60% of the desired, overall depth of the well. The ferric chloride is removed from the surface of the stent 10 via spinning, rotating, shaking or other removal methods to halt the surface-etching process. A small quantity of ferric chloride remains within the well, continuing to etch the walls of the well. The below-surface pore size and volume ares thereby increased.

Once the desired pore profile is attained, the remaining ferric chloride solution is completely removed from the pore 30 via spinning, rotating, shaking or other removal methods to stop the etching process. The stent 10 is then rinsed in methylene chloride or other similar solutions that effectively dissolve the protective coating 36 previously applied to the surface of the stent. An ultrasonic cleaning process generally follows to remove residual fluids and/or debris.

In addition to performing the above-described methods and examples on a prefabricated prosthetic device, such as a stent 10, the same processes can also be used on the individual components or raw materials of the device. For example, with regard to a stent 10, the above-described processes are performed on a flat sheet of material from which the stent filaments 22 and interconnecting components 24 are fabricated. The benefits of producing depots 30 on the raw materials prior to stent 10 assembly include increased manufacturing produtctivity, reduced fabrication costs, improved processing times and facilitated manufacturability.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of forming depots on an implantable prosthesis comprising:
    providing a prosthesis having a surface applying
    applying a first fluid onto said surface, said first fluid forming a protective coating on said surface;
    generating a mask having transparent and opaque areas, said transparent areas representing said depots;
    illuminating said mask, wherein a light passes through said transparent areas forming exposed metal areas on said surface of said prosthesis;
    applying a second fluid to said prosthesis, wherein said second fluid dissolves said exposed metal areas to a predetermined depth, forming depots;
    removing said second fluid so that a quantity of said fluid remains within said depots, said fluid expanding the size and volume of said depots so as to provide conically shaped depots having a closed end and an open end, wherein the diameter of the open end is smaller than the diameter of the closed end;
    removing said quantity of said second fluid; and
    rinsing said prosthesis in a third fluid to remove said protective coating.

2. The method according to claim 1, wherein during said act of illuminating said mask said first fluid undergoes a photochemical reaction.

3. The method according to claim 1, wherein said first fluid forms a photoresist coating.

4. The method according to claim 1, wherein said second fluid is a ferric chloride solution.

5. The method according to claim 1, wherein said third fluid is methylene chloride.

6. The method according to claim 1, wherein said light is ultraviolet light.

7. The method according to claim 1, wherein said light is laser light.

8. The method according to claim 7, wherein said laser light is generated from an excimer laser.

9. The method according to claim 1, wherein said depots are evenly distributed throughout the body of said prosthesis and the volume of said depots is generally the same.

10. The method according to claim 1, wherein the volume of each of said depots is greater at the ends of said prosthesis as compared to the midsection of said prosthesis.

11. A method for forming depots on an implantable prosthesis, comprising:
    providing a prosthesis having a surface;
    applying a first fluid onto said surface, said first fluid forming a protective coating on said surface;
    selectively ablating portions of said protective coating with a laser;
    drilling into said prosthesis with said laser to form depots;
    applying a second fluid to said prosthesis, wherein said second fluid expands the size and volume of said depots to provide a conically shaped depot having an open end and a closed end, wherein the diameter of the closed end is larger than the diameter of the open end;
    removing said second fluid; and
    rinsing said prosthesis in a third fluid to remove said protective coating.

12. The method according to claim 11, wherein said laser is an UV laser.

13. The method according to claim 11, wherein said laser is an excimer laser.

14. The method according to claim 11, wherein said laser is a Nd:YAG laser.

15. The method according to claim 11, wherein the volume of each of said depots is greater at the ends of said prosthesis as compared to the midsection of said prosthesis.

* * * * *